United States Patent [19]

Marvel et al.

[11] 4,073,291

[45] Feb. 14, 1978

[54] TOPICAL DEVICE FOR ADMINISTERING TRETINOIN

[75] Inventors: John R. Marvel; James A. Mezick, both of East Brunswick, N.J.

[73] Assignee: Johnson & Johnson, New Brunswick, N.J.

[21] Appl. No.: 709,370

[22] Filed: July 28, 1976

[51] Int. Cl.² .............................................. A61F 13/02
[52] U.S. Cl. .................................. 128/155; 128/260; 128/268; 424/28
[58] Field of Search .................. 424/28; 128/155, 260, 128/268

[56] References Cited

U.S. PATENT DOCUMENTS 3,896,789  7/1975  Trancik ............................. 128/268 X

*Primary Examiner*—Benjamin R. Padgett
*Assistant Examiner*—E. Suzanne Parr

[57] ABSTRACT

Tretinoin is incorporated in the adhesive mass of a dermatologically acceptable pressure-sensitive adhesive tape for the localized topical treatment of such skin conditions as acne and warts.

10 Claims, No Drawings

TOPICAL DEVICE FOR ADMINISTERING TRETINOIN

BACKGROUND OF THE INVENTION

1. Field of the Invention

The invention relates to dermatologically acceptable pressure sensitive tape containing uniformly dispersed within the adhesive mass an effective, releasable concentration of tretinoin (all trans-retinoic acid, or Vitamin A acid). More particularly, it relates to an adhesive tape comprising a flexible backing having a dermatologically acceptable pressure sensitive adhesive mass coated on one side of said backing, this adhesive mass being compatible with, and containing uniformly distributed therethrough, a therapeutically effective concentration of tretinoin. This product is particularly advantageous for treating such dermatological disorders as warts and localized episodes of acne vulgaris.

2. Description of the Prior Art

It has been demonstrated that prolonged topical application of Tretinoin (Vitamin A acid) is effective in the treatment of acne (Kligman, A. M., "Topical Vitamin A acid in Acne Vulgaris", *Arch Derm.*, 99: 469–476 April 1969). Kligman utilizes a composition in which Vitamin A acid is dispersed in a water-miscible (substantially oil- and fat-free) liquid carrier having high solvating action. The topical application of this Vitamin A acid composition causes irritation of the skin in the treated areas. See U.S. Pat. No. 3,729,568 issued Apr. 24, 1973, to Albert M. Kligman. It has also been reported that tretinoin is effective in the topical treatment of such other skin conditions as warts. (Lester, R. et al.: *Arch Derm.* 104: 330, 1971).

It has also been found that tretinoin can be supplied in effective topical doses from cream or gel formulations containing suitable concentrations of tretinoin. A cream formulation is generally more acceptable to patients than the liquid vehicle from the point of view of aesthetics and ease of application. Moreover, another important advantage of the cream form of tretinoin is that it reduces the side effects normally associated with the topical application of tretinoin. These side effects, erythema, stinging and itching, may be sufficient to cause the patient to discontinue the application of tretinoin before it can be fully effective upon the condition being treated.

Notwithstanding these advantages, cream formulations containing tretinoin possess some undesirable attributes. One of these undesirable attributes is the difficulty in uniformly applying sufficient amounts of the active ingredient to the lesion being treated to be effective and at the same time avoid local excesses, surface spread or pooling into facial creases, the nasolabial folds and corners of the mouth where the cream may cause erythema, stinging and itching. Another undesirable attribute of cream formulations of tretinoin is their relative instability, often necessitating the use of refrigeration or antimicrobial preservatives to prevent microbiological contamination, as well as special additives to maintain physical stability. One way of overcoming some or all of these undesirable attributes is by using gel formulations.

Occlusive dressings have been found to promote penetration of tretinoin through the skin. Occlusion also tends to keep warts moist, and prior wart treatments have been found to be more effective on wet warts than on dry warts.

U.S. Pat. No. 3,632,740, issued Jan. 4, 1972, discloses uniformly dispersing a topical corticosteroid in the pressure-sensitive adhesive coating of an adhesive tape for use in topical steroid therapy.

SUMMARY OF THE INVENTION

We have found that tretinoin can be incorporated in a wide range of concentrations in commonly used, dermatologically acceptable pressure-sensitive adhesive masses, such as the acrylic based adhesive masses, that are compatible with tretinoin. When these masses are then spread on a flexible backing to form an adhesive tape and the tape is applied to the skin, the tretinoin retains its biological activity and is readily released from the tape for absorption through the skin for sustained periods of time. The fact that tretinoin, which is an unsaturated compound that tends to degrade or polymerize at ambient temperatures and is sensitive to ultraviolet light, could be incorporated in such adhesive masses without losing its activity, and could be released from such masses in therapeutic levels over sustained periods while in contact with the skin, is a surprising discovery which affords additional flexibility to the physician and patient in the treatment of a variety of dermatological conditions that are responsive to tretinoin therapy. It is believed that the tapes of the present invention will have particular application to the treatment of warts and certain localized acne lesions. As is believed apparent from the foregoing discussion, by the expression "adhesive masses that are compatible with tretinoin" we mean that the adhesive mass in which the tretinoin is incorporated is essentially inert to the tretinoin, in that it does not materially degrade the tretinoin nor otherwise significantly interfere with its ability to be released from the mass in therapeutically active form when the adhesive mass is placed in contact with the skin of a mammal.

DESCRIPTION OF THE PREFERRED EMBODIMENTS

The present invention provides a therapeutic device which comprises a flexible backing having coated thereon a dermatologically acceptable pressure-sensitive adhesive which is compatible with tretinoin, this adhesive mass having distributed therethrough a therapeutically effective amount of tretinoin. In a preferred embodiment, the device is an occlusive adhesive tape wherein the backing is a synthetic organic film comprising, for example, polyethylene, and the adhesive mass comprises an acrylate pressure-sensitive adhesive. Since tretinoin has been indicated as therapeutic for a variety of dermatological conditions, and each of these conditions may vary in severity, it is contemplated that the concentration of the tretinoin in the adhesive mass may be varied as desired to meet medical needs. Generally, however, the concentration will be such that there will be at least about 2 mg. of tretinoin per square foot of tape. This is approximately equivalent to the amount of tretinoin which is deposited on the skin by applying a cream base containing a 0.05 wt. % concentration of tretinoin. As indicated, some conditions may call for lower concentrations of tretinoin, whereas for other conditions higher concentrations up to about 22 mg per square foot may be desirable. A typical concentration may be 16 micrograms per $cm^2$.

The tretinoin should be incorporated into the pressure-sensitive adhesive in such a manner that it is thoroughly and completely dispersed throughout the entire pressure-sensitive adhesive. It was found that this can best be done by first dissolving the tretinoin in a liquid solvent therefor such, for example, as ethyl acetate and mixtures of ethyl acetate and cyclohexane, and then thoroughly blending the same with the pressure-sensitive adhesive composition.

If the solvent employed in the adhesive mass is also a solvent for tretinoin, the tretinoin powder may be incorporated directly into the wet adhesive mass by adding the dry treinoin powder and thoroughly mixing.

When incorporating the tretinoin into a rubber base adhesive, it is generally preferred to first formulate the adhesive mass and then to slurry or dissolve the same in a solvent medium to which is then added a solution of the tretinoin to assure complete dispersion of the tretinoin throughout the adhesive. The adhesive is then solvent spread on a backing, the solvent thereafter being evaporated. If desired, a moisture vapor pervious tape may be prepared. This may be done by perforating the tape after spreading the adhesive, by using a pervious backing and a pervious adhesive such for example as obtained by an open pattern spread or by any other method. In some applications, however, such as the treatment of warts, it may be preferable to have an impervious backing so as to promote hydration of the lesion.

As the purpose of the backing is primarily to form a support for the pressure-sensitive adhesive film, substantially any flexible backing material may be used. These include fabrics, both woven and nonwoven, paper, thin metal foil, and organic films, the most commonly used films being those formed of plasticized polyvinyl chloride, cellophane, Mylar, polyethylene and polypropylene. Naturally, when there is a particular purpose to having the backing be either occlusive or non-occlusive, the backing will be selected accordingly.

The pressure-sensitive adhesives most generally used for skin application are the rubber based pressure-sensitive adhesives, the polyvinyl alkyl ether pressure-sensitive adhesives and the acrylate pressure-sensitive adhesives. These adhesives are well known to those skilled in the pressure-sensitive adhesive art and differ from each other primarily in the type of base polymer used in preparing the same. The terminology rubber base, polyvinyl alkyl ether base and acrylate pressure-sensitive adhesive is used to indicate that the major portion of base polymer, i.e., over 50% by weight in the pressure-sensitive adhesive, is rubber, polyvinyl alkyl ether or an acrylate ester, e.g. an alkyl acrylate, polymer. Rubber base, polyvinyl ether base and acrylate base pressure-sensitive adhesives are discussed, for example, in the section "Adhesive Tapes" by C. W. Bemmels, beginning on page 585 in the Handbook of Adhesives, edited by Irving Skeist, Reinhold Publishing Co., 1962. Also, numerous acrylate pressure-sensitive adhesives are described, for example, in U.S. Pat. Nos. 3,008,850 and Re. No. 24,906 and British Pat. No. 951,428.

While the concentration of the tretinoin in the adhesive mass may vary widely, depending on the condition to be treated, its severity, etc. it is generally desirable to maintain the concentration equivalent to that obtained by spreading on the skin a cream vehicle containing a concentration of from about 0.05 wt. % to about 0.5 wt. % tretinoin. We have determined that this is equivalent, in terms of amount per unit area, to about 23.3 mg/m$^2$ and 233 mg/m$^2$, respectively.

EXAMPLE I

A. "0.5% Tretinoin Tape"

200 mg. of tretinoin were added to 70.875 g. of wet acrylate pressure-sensitive adhesive mass and mixed thoroughly.

B. "0.05% Tretinoin Tape"

20 mg. of tretinoin were added to another 70.785 g. portion of the same wet acrylate pressure-sensitive adhesive mass as used for sample A, again with thorough mixing.

C. The Acrylate Pressure Sensitive Adhesive Mass

The wet adhesive mass described in parts A and B above was prepared by reacting:
  300 parts by weight of 2-ethylhexyl acrylate
  125 parts by weight of Vinyl acetate, and
  75 parts by weight of diacetone acrylamide
in a solvent comprising
  373.5 parts by weight of ethyl acetate and
  373.5 parts by weight of cyclohexanone, using
  1.65 parts by weight of benzoyl peroxide as
the polymerization initiator, at a temperature in the range of about 80° to 85° C.

Separate samples of wet mass A (containing 200 mg. of tretinoin) wet mass B (containing 20 mg. of tretinoin) and wet mass C (control - the wet mass without and tretinoin added) were cast on silicone treated release paper in such manner that, when the solvent was evaporated, approximately one ounce of "dry" mass covered 1 yd$^2$ of release paper. It was calculated that the dry mass thus cast from sample A contained 0.71% by weight tretinoin and that cast from sample B contained 0.071% by weight tretinoin.

Then the cast masses were transfer coated onto polyethylene film backings to form tretinoin tapes "A", "B" and "C", respectively.

Four one inch square samples of tape "A" were separately extracted with 50 ml. of acetone and the tretinoin content was determined by means of a Beckman DB-G spectrophotometer. The results were as follows:

| Sample | Mg. Tretinoin/in$^2$ Tape |
|---|---|
| 1 | 0.094 |
| 2 | 0.103 |
| 3 | 0.105 |
| 4 | 0.107 |
| Average | 0.102 |

EXAMPLE II

To ascertain the extent of release of tretinoin from the tapes prepared in Example I when applied to mammalian skin, the following test was performed on five rabbits.

The backs of five rabbits were depilated with NAIR*. Two one-inch squares of each tape, A, B and C from Example 1, were randomized over the prepared backs of each rabbit. After a light Stockinette* was used to overwrap the bodies of the animals, the latter were immobilized in Draize type restrainers for twenty-four hours. At the end of that time, the skin reactions at the application sites were graded.

*Trademark

Results:
The irritation grades were as follows:

| RABBIT NO. | SAMPLE | ERYTHEMA UPON REMOVAL | ESCHAR - 72 HOURS LATER |
|---|---|---|---|
|   |   | 0.5+ | 0.5+ |
|   | A | 0.5+ | 0.5+ |
|   |   | 0.5+ | 0.5+ |
| 1 | B | 0.5+ | 0.5+ |
|   |   | 0.5+ | 0 |
|   | C | 0.5+ | 0 |
|   |   | 0.5+ | 0 |
|   | A | 0.5+ | 0 |
|   |   | 0.5+ | 0 |
| 2 | B | 0.5+ | 0 |
|   |   | 0.5+ | 0 |
|   | C | 0.5+ | 0 |
|   |   | 1.5+ | 1.0+ |
|   | A | 1.5+ | 1.0+ |
|   |   | 0.5+ | 0.5+ |
| 3 | B | 0.5+ | 0.5+ |
|   |   | 1.0+ | 0.5+ |
|   | C | 1.0+ | 0.5+ |
|   |   | 2.0+ | 2.0+ |
|   | A | 2.0+ | 2.0+ |
|   |   | 1.0+ | 1.0+ |
| 4 | B | 1.0+ | 1.0+ |
|   |   | 0.5+ | 0.5+ |
|   | C | 0.5+ | 0.5+ |
|   |   | 1.5+ | UNABLE TO EVALUATE- EXCESSIVE HAIR GROWTH |
|   | A | 1.5+ | " |
|   |   | 1.0+ | " |
| 5 | B | 1.0+ | " |
|   |   | 0.5+ | " |
|   | C | 0.5+ |   |

Note: Grades could range from Minimum of 0 to maximum of 4+.
Conclusion: The degree of skin irritation produced by the tape samples was roughly proportional to the concentration of tretinoin in the adhesive mass.

While the tretinoin gel compositions of the present invention have been described herein primarily as suitable for use in treating acne and warts, it will be understood that these compositions are effective generally for treating dermatological conditions where tretinoin is indicated.

As will be obvious to those skilled in the art, many variations and modifications may be made without departing from the spirit and scope of the invention.

What is claimed is:

1. A therapeutic device comprising a flexible backing having coated thereon a dermatologically acceptable pressure-sensitive adhesive which is compatible with, and has uniformly distributed therein, a therapeutically effective amount of tretinoin.

2. A therapeutic device of claim 1 comprising a flexible backing having a pressure-sensitive adhesive coated thereon, said pressure-sensitive adhesive being compatible with, and having uniformly dispersed therein, a therapeutically effective amount of tretinoin and being selected from the group consisting of rubber based pressure-sensitive adhesives, polyvinyl alkyl ether based pressure sensitive adhesives and acrylate pressure-sensitive adhesives.

3. A therapeutic device of claim 1 in which said pressure-sensitive adhesive is acrylate pressure-sensitive adhesive.

4. A therapeutic device of claim 1 in which said treinoin is present in an amount of at least about 2 milligrams per square foot.

5. A therapeutic device of claim 4 in which said pressure-sensitive adhesive is an acrylate pressure-sensitive adhesive.

6. A therapeutic device of claim 1 comprising a transparent flexible backing, a transparent acrylate pressure-sensitive adhesive coating on said backing, said pressure-sensitive adhesive coating containing a therapeutically effective amount of tretinoin uniformly dispersed therethrough.

7. A therapeutic device of claim 4 in which the amount of said tretinoin is between about 2 milligrams and about 22 milligrams per square foot.

8. A pressure sensitive adhesive tape comprising a flexible backing having a pressure sensitive interpolymer of an acrylate ester adhesive coating on said backing, said pressure sensitive coating containing a therapeutic amount of tretinoin uniformly distributed therein.

9. A therapeutic device of claim 5 in which said flexible backing comprises polyethylene.

10. A therapeutic device of claim 6 in which said flexible backing comprises polyethylene.

* * * * *